United States Patent
Benner et al.

(10) Patent No.: US 10,865,431 B1
(45) Date of Patent: *Dec. 15, 2020

(54) POLYMERASE INCORPORATION OF NON-STANDARD NUCLEOTIDES

(71) Applicants: Steven A Benner, Gainesville, FL (US); Zunyi Yang, Gainesville, FL (US)

(72) Inventors: Steven A Benner, Gainesville, FL (US); Zunyi Yang, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/997,339

(22) Filed: Jun. 4, 2018

Related U.S. Application Data

(63) Continuation-in-part of application No. 14/218,405, filed on Mar. 18, 2014, now Pat. No. 9,988,659, which is a continuation of application No. 12/653,613, filed on Dec. 16, 2009, now Pat. No. 9,334,534, which is a continuation-in-part of application No. 12/999,138, filed as application No. PCT/US2009/003595 on Jun. 16, 2009, now Pat. No. 8,614,072.

(60) Provisional application No. 61/802,913, filed on Mar. 18, 2013, provisional application No. 61/132,225, filed on Jun. 17, 2008.

(51) Int. Cl.
   *C12P 19/34* (2006.01)
   *C12Q 1/6869* (2018.01)
   *C07H 21/04* (2006.01)
   *C12Q 1/6844* (2018.01)

(52) U.S. Cl.
   CPC .............. *C12P 19/34* (2013.01); *C07H 21/04* (2013.01); *C12Q 1/6844* (2013.01); *C12Q 1/6869* (2013.01); *C12Q 2521/101* (2013.01); *C12Q 2525/117* (2013.01)

(58) Field of Classification Search
   CPC .................................................... C12P 19/34
   USPC ......................................................... 435/6.1
   See application file for complete search history.

(56) References Cited

U.S. PATENT DOCUMENTS 8,614,072 B2 * 12/2013 Benner .................. C12Q 1/686
   435/6.1
9,334,534 B1    5/2016 Benner 2007/0087361 A1 * 4/2007 Grenier ................ C12Q 1/6823
   435/6.18
2007/0105099 A1 * 5/2007 Prudent ................ C12Q 1/6844
   435/6.1
2008/0108124 A1 * 5/2008 Moser ...................... C12Q 1/48
   435/184

OTHER PUBLICATIONS

Brownie J. 1997 The elimination of primer-dimer accumulation in PCR. Nucleic Acids Res. 25, 3235-3241.
Horlacher J. 1995 Recognition by viral and cellular DNA polymerases of nucleosides bearing bases with non-standard hydrogen bonding patterns. Proc. Natl. Acad. Sci., 92, 6329-6333.
Hutter D 2003 ) Expanding the genetic alphabet. Non-epimerizing nucleoside with the pyDDA hydrogen bonding pattern. J. Org. Chem., 68, 9839-9842.
Switzer C Y 1989 Enzymatic incorporation of a new base pair into DNA and RNA. J. Am. Chem. Soc. 111, 8322-8323.
Voegel J J 1996 Synthesis and characterization of non-standard nucleosides and nucleotides bearing the acceptor-donor-donor pyrimidine analog 6-amino-3-methylpyrazin-2-one. Helv. Chim. Acta 79, 1863-1880.
Voegel JJ 1996 Synthesis, molecular recognition & enzymology of oligonucleotides containing the non-standard base pair between 5-aza-7-deaza-iso-guanine & 6-amino-3-methyipyrazin-2-one, a donor-acceptor-acceptor purine analog and an acceptor-donor-donor pyrimidine analog. Helv. Chim. Acta 79, 1881-1898.
Von Krosigk U 1995 pH-independent triple helix formation by an oligonucleotide containing a pyrazine donor-donor-acceptor base. J. Am. Chem. Soc. 117, 5361-5362.
Yang Z 2006 Artificially expanded genetic information system. A new base pair with an alternative hydrogen bonding pattern. Nucleic Acids Res., 34, 6095-6101.
Yang Z 2007 Enzymatic incorporation of a third nucleobase pair. Nucl. Acids Res. 35, 4238-4249.

* cited by examiner

*Primary Examiner* — Jezia Riley

(57) ABSTRACT

The disclosed invention teaches processes to create a Watson-Crick complementary copy of a preselected oligonucleotide that contain non-standard nucleotides, which form nucleobase pairs fitting the standard Watson-Crick geometry, but here said pairs are joined by hydrogen bonding patterns different from those that join standard A:T and G:C pairs. The invention further relates to polymerases that incorporate those non-standard nucleotide analogs into oligonucleotide products using the corresponding triphosphate derivatives.

13 Claims, 8 Drawing Sheets

Specification includes a Sequence Listing.

POLYMERASE INCORPORATION OF NON-STANDARD NUCLEOTIDES

CROSS REFERENCE TO RELATED APPLICATIONS

This application is a continuation-in-part of U.S. patent application Ser. No. 14/218,405, currently pending, entitled "In Vivo Conversion of Nucleosides in Plasmid DNA". U.S. patent application Ser. No. 14/218,405 was a continuation-in-part of U.S. patent application Ser. No. 12/653,613, filed Dec. 16, 2009, entitled "Processes replacing standard nucleotides by non-standard nucleotides and non-standard nucleotides by standard nucleotides in DNA, now issued as U.S. Pat. No. 9,334,534. U.S. patent application Ser. No. 12/653,613 was a continuation-in-part of U.S. patent application Ser. No. 12/999,138, which became U.S. Pat. No. 8,614,072, entitled "Polymerase Incorporation of Non-standard Nucleotides", which was filed on Jun. 16, 2009 as the US national application of PCT/US2009/003595. U.S. Ser. No. 12/999,138 claimed the benefit of U.S. Provisional Patent Application 61/132,225, which was filed on Jun. 17, 2008. U.S. patent application Ser. No. 14/218,405 claims priority to U.S. provisional patent application 61/802,913, entitled "In vivo conversion of nucleosides in plasmid DNA", which was filed Mar. 18, 2013.

STATEMENT OF RIGHTS TO INVENTIONS MADE UNDER FEDERALLY-SPONSORED RESEARCH

None.

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION

Background of the Invention

1. Field of the Invention

This invention relates to processes that copy oligonucleotides in a poymerase chain reaction (PCR) where these oligonucleotides incorporate nucleotide analogs ("non-standard nucletides") that form base pairs joined by hydrogen bonding patterns not found in standard nucleotides A, T, G and C. The invention relates more specifically to processes that amplify oligonucleotides holding more than one non-standard nucleotides, including non-standard nucleotides at adjacent positions in the oligonucleotides chain, and amplification in a nested PCR format.

2. Description of Related Art

Natural oligonucleotides bind to complementary oligonucleotides according to well-known rules of nucleobase pairing first elaborated by Watson and Crick, where adenine (A) pairs with thymine (T) (or uracil, U, in RNA), and guanine (G) pairs with cytosine (C), with anti-parallel complementary strands. In this disclosure, "DNA". "oligonucleotide", or "nucleic acid" is understood to include DNA and RNA, as well as derivatives where the sugar is modified, as in 2'-O-methyl and 2',3'-dideoxynucleoside derivatives, where the nucleobase has an appendage, and these nucleic acids and their analogs in non-linear topologies, including as dendrimers, comb-structures, and nanostructures, and analogs carrying appendages or tags (e.g., fluorescent, functionalized, or binding, such as biotin). Further, "polymerase" in this application is meant to include DNA polymerases of all families, RNA polymerases, and reverse transcriptases.

These pairing rules allow specific hybridization of oligonucleotides to complementary oligonucleotides, making oligonucleotides valuable as probes in the laboratory, in diagnostics, as messages that direct the synthesis of proteins, and in other applications known in the art. Such pairing is used, for example and without limitation, to capture oligonucleotides to beads, arrays, and other solid supports, allow nucleic acids to fold in hairpins, beacons, and catalysts, support function, such as fluorescence, quenching, binding/capture, and catalysis, and as part of complex structures, including dendrimers and nanostructures, and scaffolds to guide chemical reactions.

Further, base pairing underlies the enzymatic synthesis of oligonuleotides complementary to a template. Here, assembly of building blocks from nucleoside triphosphates is directed by a template to form a complementary oligonucleotide with a complementary sequence. This is the basis for replication in living systems, and underlies technologies for enzymatic synthesis and amplification of specific nucleic acids by enzymes such as DNA and IA polymerase, the polymerase chain reaction (PCR), and assays involving synthesis, ligation, cleavage, immobilization and release, inter alia.

Watson-Crick pairing rules can be understood as the product of two rules of complementarity: (1) size complementarity (a big purine pairs with a small pyrimidine) and (2) hydrogen bonding complementarity (hydrogen bond donors pair with hydrogen bond acceptors). However, as noted by U.S. Pat. Nos. 5,432,272, 5,965,364, 6,001,983, 6,037,120, 6,140,496, 6,627,456, and 6,617,106, Watson-Crick geometry can accommodate as many as 12 nucleobases forming 6 mutually exclusive pairs. Of these, four nucleobases forming two pairs are designated "standard", while eight nucleobases forming four pairs were termed "non-standard", and may be part of an "artificially expanded genetic information system" (AEGIS).

To systematize the nomenclature for the hydrogen bonding patterns, the hydrogen bonding pattern implemented on a small component of a nucleobase pair are designated by the prefix "py" Following this prefix is the order, from the major to the minor groove, of hydrogen bond acceptor (A) and donor (D) groups. Thus, both thymine and uracil implement the standard hydrogen bonding pattern pyADA. The standard nucleobase cytosine implements the standard hydrogen bonding pattern pyDAA. Hydrogen bonding patterns implemented on the large component of the nucleobase pair are designated by the prefix "pu". Following the prefix, hydrogen bond donor and acceptor groups are designated, from major to minor groove, by "A" and "D". Thus, the standard nucleobases adenine and guanine implement the standard hydrogen bonding patterns puDA- and puADD respectively.

A central teaching of this disclosure is that hydrogen-bonding patterns are distinct from the organic molecule that implemented them. Thus, guanosine implements the puADD hydrogen-bonding pattern. So does, however, 7-deazaguanosine, 3,7-dideazaguanosine, and many other purines and purine analogs, including those that carry side chains carrying functional groups, such as biotin, fluorescent, and quencher groups. Which organic molecule is chosen to implement a specific hydrogen-bonding pattern determines, in part, the utility of the non-standard hydrogen-bonding pattern, in various applications to which it might be applied.

Claims of U.S. Pat. No. 5,432,272 and its successors covered non-standard bases that implemented the pyDDA hydrogen bonding pattern. Subsequent efforts to use these, however, encountered problems, including epimerization [Voe96a,b], oxidation [Von95], and uncharacterized decomposition. Accordingly, Benner invented a new non-standard nucleoside, 6-amino-5-nitro-3-(1'-beta-D-2'-deoxyribofuranosyl)-2(1H)-pyridone (dZ) to implement the pyDDA hydrogen bonding pattern. The nitro group rendered the otherwise electron-rich heterocycle stable against both oxidation and epimerization under standard conditions. When paired with a corresponding puAAD nucleotide, duplexes were formed with stabilities that, in many cases, were higher than those observed in comparable strands incorporating the dG:dC nucleobase pair [Yan06]. This invention is covered by U.S. patent application Ser. No. 11/372,400, which is incorporated herein by reference. Contents of this patent application have been published [Hut03].

While Z supports binding of oligonucleotides containing it to complementary strands that match a nucleobase implementing the puAAD hydrogen bond pattern, it was not clear that polymerases would accept this unnatural base pair. Polymerases are known to be idiosyncratic [Hor95], meaning that experimentation is necessary to ascertain whether a specific implementation of a non-standard hydrogen bonding scheme can be accepted by a polymerase.

Thus, it was necessary to show by experiment that polymerases could incorporate dZ and dP. This was done for oligonucleotides containing a single dZ or dP [Yan07], which was published less than a year before the priority date of the instant application. However, [Yan07] showed that the dZ and dP are lost in multiple PCR cycles with Taq and Deep Vent (exo–) polymerases, perhaps via a mechanism where deprotonated dZ mispairs with dG (or deprotonated dG pairs with dZ), while protonated dC mispairs with dP (or protonated dP pairs with dC). Thus, this art teaches away from any use of the non-standard dZ:dP nucleobase pair in higher level PCR, defined as PCR that creates amplicons with multiple non-standard nucleotides.

BRIEF SUMMARY OF THE INVENTION

This invention is a process that makes a single copy of an oligonucleotide containing one or more non-standard nucleotides (FIG. 1). That process exploits an oligonucleotide having a preselected sequence. This oligonucleotide serves as a template that is to be copied. This template contains one or more nonstandard nucleotides within its preselected sequence. The process also exploits a second oligonucleotide that serves as a primer. This primer binds at or near the 3'-end of that template, leaving as a single-strand portion of that template that is not bound 20 complement. The primer binds to a portion of the template by exploiting Watson-Crick pairing, were not only does A pair with T and G pair with C but also, optionally, nonstandard nucleotides in the template pair with nonstandard nucleotides in the primer using extended Watson-Crick pairing rules as described in FIG. 1. Experimentally, the binding between with primer and the template is most preferably achieved by annealing the two single-stranded oligonucleotides in aqueous solution by lowering the temperature from a high temperature with the two do not bind to each other, to a lower temperature where the two do bind, said annealing process being well known in the art for natural DNA. The process is then completed by a contacting in aqueous solution the annealed complex with triphosphates that are complementary, again in the Watson-Crick sense, to the nucleotides in the single-stranded portion of the template-primer complex, together with a polymerase that extends the primer by adding nucleotides by a process well known in the art that matches incoming triphosphates to their complementary Watson-Crick nucleotide in the template. Said matching again follows the extended Watson-Crick pairing rules described in FIG. 1. The presently preferred pH is between 6.5 and 7.5.

DETAILED DESCRIPTION OF THE INVENTION

Figure 1:
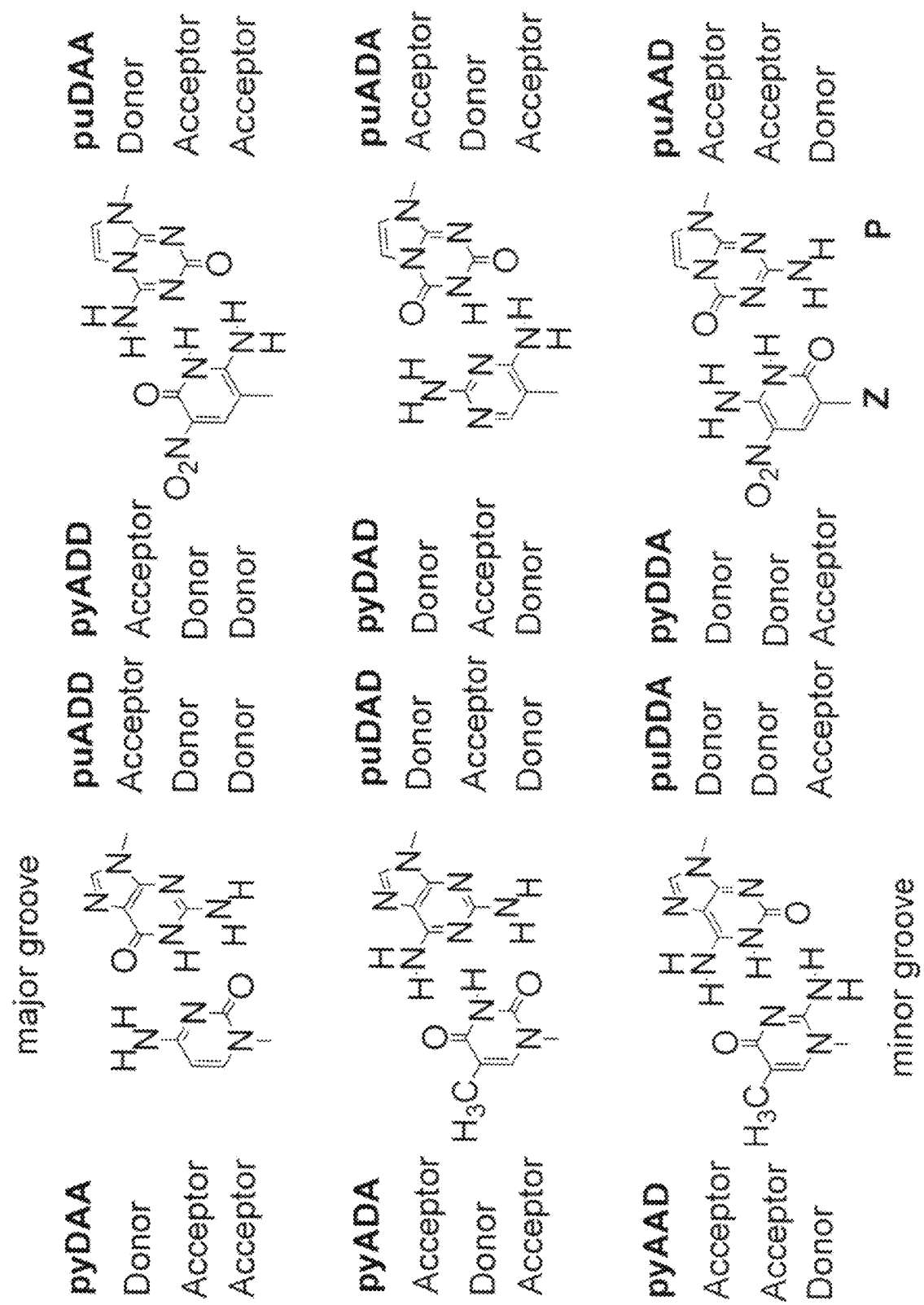
FIG. 1. A set of heterocycles implementing a set of hydrogen bonding patterns. The heterocycles most preferably used in the processes of the instant invention are labeled dZ and dP. The bond extending down from each of the pyrimidines or pyrimidine analog heterocycles, and the bond extending down to the right from each of the purine or purine analog heterocycles, is a bond attaching that heterocycle to the ribose or deoxyribose of the oligonucleotide.

By way of U.S. patent application Ser. No. 14/218,405, and U.S. patent application Ser. No. 12/653,613, filed Dec. 16, 2009, this application is a continuation-in-part of U.S. patent application Ser. No. 12/999,138, now U.S. Pat. No.

8,614,072, which was the US national application of PCT/US2009003595. That PCI application, and the corresponding U.S. patent application Ser. No. 12/999,138, including their disclosures, figures, and examples, are incorporated by reference in their entirety.

6-Amino-5-nitro-3-(1'-beta-D-2'-deoxyribofuranosyl)-2(1H)-pyridone (trivially called dZ), its protected phosphoramidite derivatives suitable for chemical oligonucleotides synthesis, its triphosphate and its thiotriphosphate are reported in U.S. patent application Ser. No. 11/372,400 and in [Hut03], both of which are incorporated herein by reference, especially those portions that describes the synthesis, purification, and analysis of these products, and their use in oligonucleotide synthesis.

The complement of dZ, 2-amino-8-(1'-beta-D-2'-deoxyribofuranosyl)-imidazo[1,2-a]-1,3,5-triazin-4(8H)-one (implementing puAAD, trivially called dP) and these same derivative, are reported in [Hut03][Yan06]. These references are also both incorporated herein by reference, especially those portions that describe synthesis, purification, an analysis of these products, and their use oligonucleotide synthesis. These are preferred as non-standard nucleotides in the instant invention.

It is known from the parent U.S. application Ser. No. 12/999,138 and from the art [Yan07], PCR amplification is possible for oligonucleotides that contain a single dP nucleotide or a single dZ nucleotide in the amplicon. However, that art shows that upon multiple PCR cycles, dP and dZ are removed from the amplicon. The essence of the Ser. No. 12/999,138 invention was the recognition it was possible to place dP and/or dZ in the PCR primers themselves. For amplification of standard oligonucleotides, the dP and dZ would not be in the region of the primer that contacts that target, but rather within an oligonucleotide tag (or tail) appended to the 5'-end of the PCR primer that does contact the standard oligonucleotide target. PCR primers having two parts, a 5'-end containing dP and/or dZ (as well as standard nucleotides, optionally) and a 3'-end that is complementary to the target, are called "chimeric primers". PCR amplification with chimeric primers can then be done in a nested fashion [Bro97], where any loss of the non-standard nucleotide is restored in a subsequence PCR cycle. After the chimeric primers are consumed in the first cycles, "external primers" having the sequence of only the 5'-tags continue the PCR.

What was not known in any art published before the priority date of the instant application, and what is not anticipatable from the prior art given the idiosyncrasies of polymerases when challenged with unnatural nucleoside triphosphate substrates [Hor95], is that PCR would succeed with amplicons that contain multiple dPs and/or multiple dZs. A key discovery, not reported in any art published before the priority date of the instant application, is that PCR can be successful when multiple dP and dZ's are present in the amplicons. Further, we disclose here for the first time certain DNA polymerases that support incorporation of adjacent dZs and adjacent dPs.

A third discovery was also unanticipated by us or the art. It turned out that by doing nested PCR with dZ and/or dP in the external primers, it was possible to obtain cleaner PCR products.

The parent Ser. No. 12/999,138 application describes and claims this amplification. The instant application claims and microscopic step of the PCR amplification, step where a single copy of the single-stranded region of the template that has been annealed to a primer is created by polymerase extension.

Example 1. Nested PCR with dZ and dP

This example demonstrates that chimeric primers containing dZ and dl in their external segments support PCR. The following oligonucleotides were prepared by phosphoramidite synthesis. These include two reverse chimeric primers, identical except that in R-36-Nest, some of the G's were replaced by P's in the segment not complementary to the template:

R-36-Std:
$$\text{SEQ ID 1}$$
3'-CCATGGTAGCTATGCGCAACGCTAGCGAGGAAGGAC-5'-P$^{32}$ R-36-Nest:
$$\text{SEQ ID 2}$$
3'-CCATGGTAGCTATGCGCAACPCTAPCGAPGAAPGAC-5'-P$^{32}$ a pair of complementary template sequences:

Temp-R-47:
$$\text{SEQ ID 3}$$
5'-CCATGGGAGACCGCGGTGGGCCCGGCCGGGTACCATCGATACGCGT T-3'

Temp-F-47:
$$\text{SEQ ID 4}$$
3'-GGTACCCTCTGGCGCCACCCGGGCCGGCCCATGGTAGCTATGCGCA A-5' and two forward chimeric primers, one with the same replacements:

$$\text{SEQ ID 5}$$
5' CTAPGACPACGPACTPCCCATGGGAGACCGCGGT-3'
(F-34-Nest)

$$\text{SEQ ID 6}$$
5'-CTAGGACGACGGACTGCCCATGGGAGACCGCGGT-3'
(F-34-Std)

The underlined portions of the primers are complementary to the template. The portions not underlined are the tags that contain non-standard nucleotides. In separate experiments the chimeric and non chimeric primers were incubated under the following conditions:

| Components | Volume (μl) | Final Concentration |
|---|---|---|
| Nuclease-Free Water (final volume of 20 μl) | 1.6 | |
| Forward Primer: F-34-Nest (2 pmol/μl) | 5 | 500 nM |
| Reverse Primer: R-36-Nest (1 pmol/μl, radio-labeled) | 1 | 50 nM |
| Reverse Primer: R-36-Nest (1.5 pmol/μl) | 6 | 450 nM |
| Template: Temp-F-47(1 pmol/μl) | 0.1 | 5 nM |
| Temp-R-47(1 pmol/μl) | for each | |
| 10 × Reaction Buffer | 2 | 1× |
| dNTP (2 mM of each dNTP) | 2 | 0.1 mM each |
| dZTP (2 mM) or Water (for negative control) | 2 | 0.1 mM |
| Taq (5 U/μl) | 0.2 | 0.05 U/μl |

Figure 3:
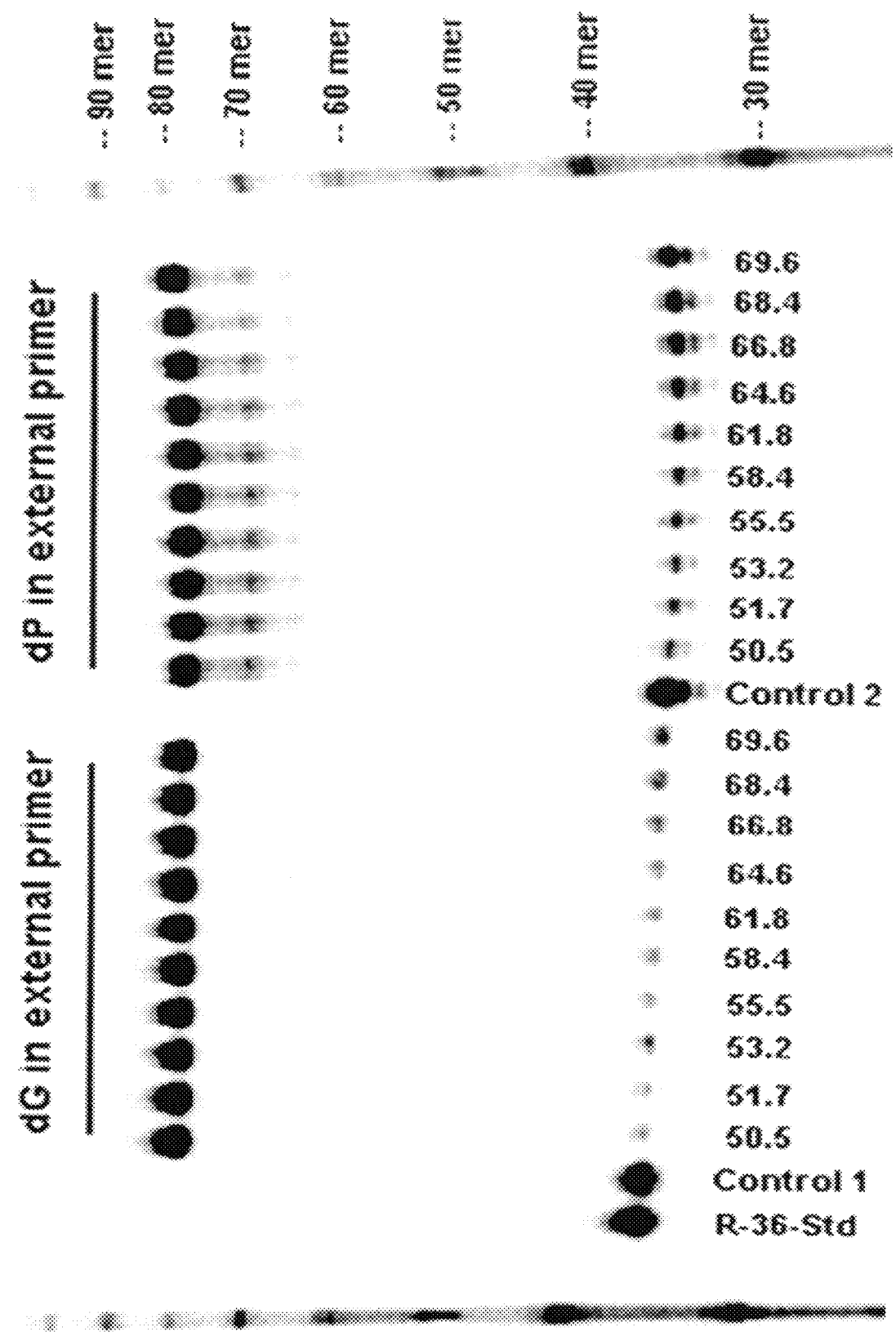
FIG. 3. Autoradiograph of an electrophoresis gel showing PCR products as described in Example 1. Left: PCR using primers only standard nucleotides in both the amplicon binding region and in the 5'-tag. Right. PCR using primers containing dP in the 5'-tag.

The products were resolved by gel electrophoresis (FIG. 3). These results show that primers containing multiple dP's support PCR works. The experiment does not show, however, that primers containing consecutive dPs effectively support PCR.

Example 2

Figure 2:
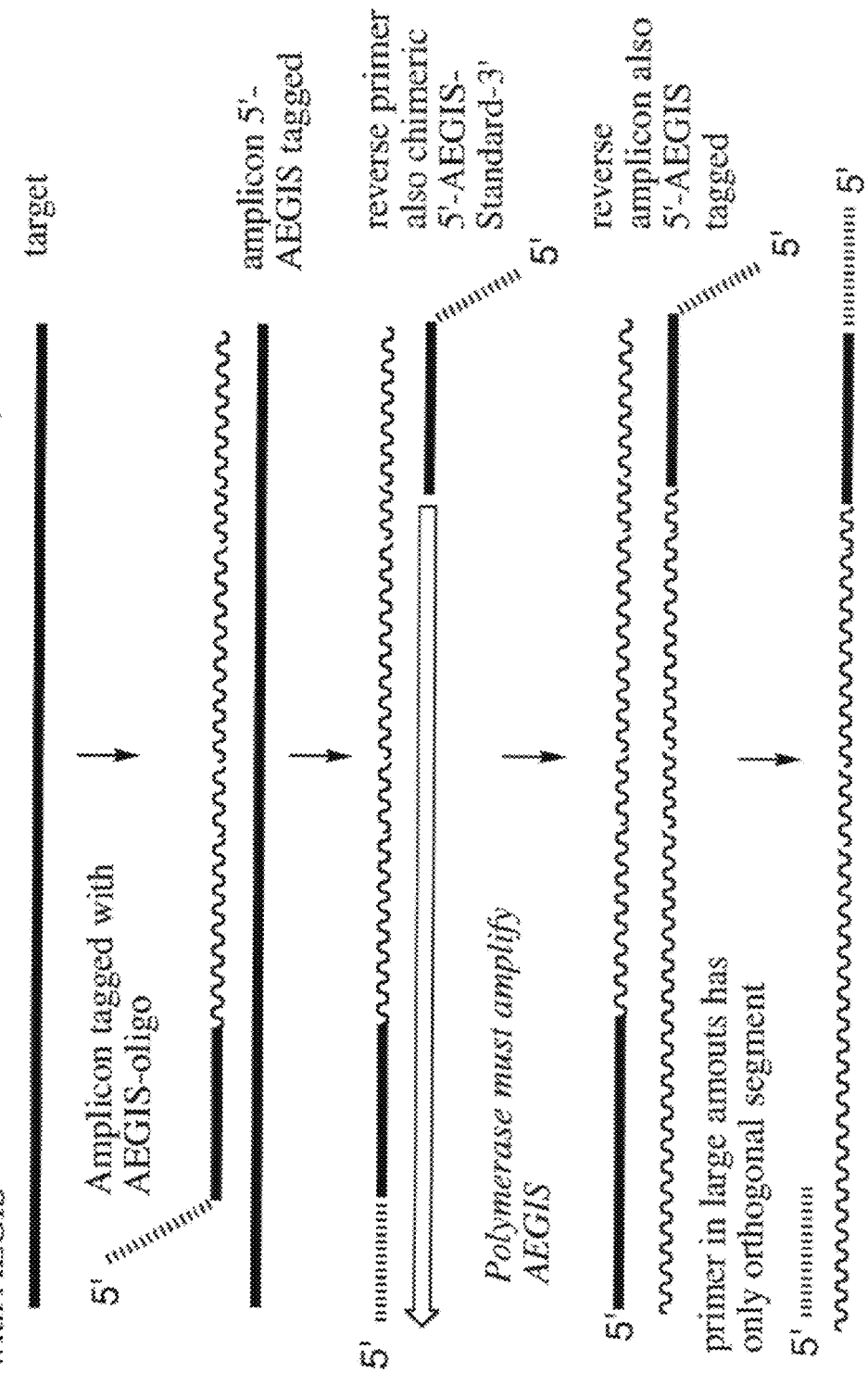
FIG. 2. Schematic showing nested PCR, where nucleotides from an artificially expanded genetic information system (AEGIS) are included in the tags (vertically hashed lines; these may also contain standard nucleotides) attached to chimeric PCR primers. The chimeric primers containing the amplicon-specific binding segments (built from standard nucleotides), which initiate the PCR, may be at low concentrations, diminishing the possibility of off-target priming. After consumption of the chimeric primers in the early rounds of PCR, the PCR is continued through priming through external primers that containing the same AEGIS-standard mixture.

This experiment demonstrated the use of dZ and dP pairing in the external segments of a nested PCR [Bro97], shown schematically in FIG. 2. The following oligonucleotides were prepared by phosphoramidite synthesis. These were set up in three set of nested PCR experiments. The first used external primers, one containing dP, the other not:

$^{32}$P-5'CTAPGACPACGPACTPC-3' F-17-Nest        SEQ ID 7

$^{32}$P-5'-CTAGGACGACGGACTGC-3' F-17-Std        SEQ ID 8 applied in a direct PCR experiment for a longer template that included Temp-R-47 in its middle:

Temp-R-81:
                                                 SEQ ID 9
5'-CTAGGACGACGGACTGCCCATGGGAGACCGCGGTGGCCCGGCCGGG
TACCATCGATACGCGTTGCGATCGCTCCTTCCTG-3' and two reverse external primers, one containing dP, the other not:

R-17-Std:
                                                 SEQ ID 10
3'-CGCTAGCGAGGAAGGAC-5'

R-17-Nest:
                                                 SEQ ID 11
3'-CPCTAPCGAPGAAPGAC-5'

These were incubated using the following procedure in Experiment A.

| Components | Volume (μl) | Final Concentration |
|---|---|---|
| Nuclease-Free Water (final volume of 20 μl) | 7.65 | |
| Forward Primer: F-17-Std or Nest (2 pmol/μl) | 2.25 | 225 nM |
| Forward Primer: R-17-Std or Nest (1 pmol/μl, radio-labeled) | 0.5 | 25 nM |
| Reverse Primer: R-17-Std or Nest (2 pmol/μl) | 2.5 | 250 nM |
| Template: Temp-R-81(0.01 pmol/μl) | 0.5 | 0.25 nM |
| 10 × Reaction Buffer | 2 | 1 × |
| (MgCl$_2$(15 mM) | | (MgCl$_2$(1.5 mM) |
| (MgCl$_2$(25 mM) | 0.4 | (MgCl$_2$(0.5 mM) |
| dNTP (2 mM of each dNTP) | 2 | 0.2 mM each |
| dZTP (2 mM) | 2 | 0.2 mM |
| Taq (5 U/μl) | 0.2 | 0.05 U/μl |

Figure 4:
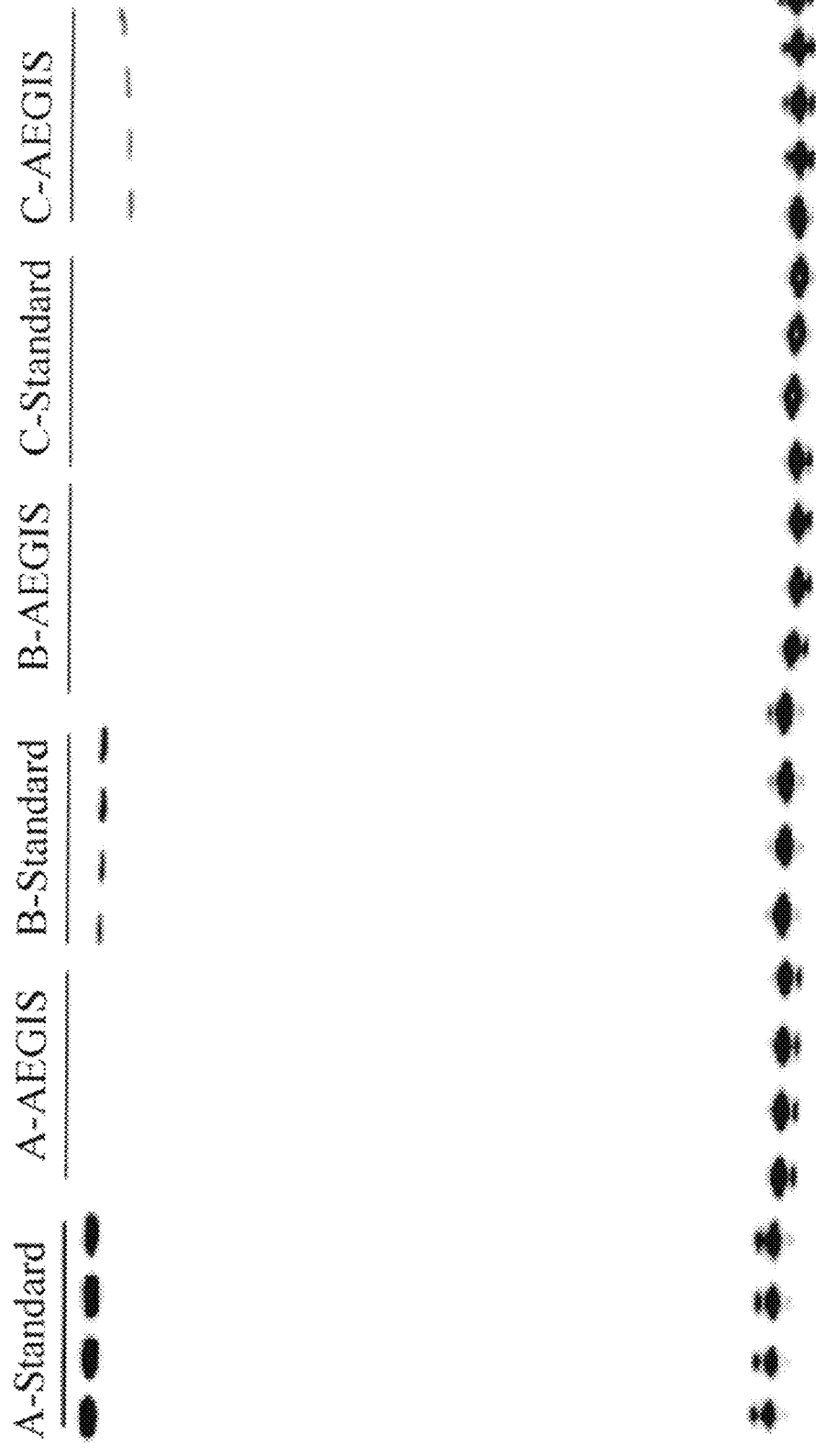
FIG. 4. Autoradiograph of an electrophoresis gel showing nested PCR products obtained as described in Example 2.

The standard primers F-17-Std and R-17-Std should amplify the Temp-R-81 target, leading to a band in a gel electrophoresis resolution that migrates as an 81-mer. This is in fact the case (FIG. 4, A-Std lane). If dP does not bind to dC, then the AEGIS dP-containing primers should not yield and 81-mer band. This is also the case (FIG. 4, A-AEGIS).

In another experiment, the following recipe was used in a nested PCR experiment:

| Components | Volume (μl) | Final Concentration |
|---|---|---|
| Nuclease-Free Water (final volume of 20 μl) | 6.65 | |
| Forward Primer: F-17-Std or Nest (2 pmol/μl) | 52.25 | 225 nM |
| Forward Primer: F-17-Std or Nest (1 pmol/μl, radio-labeled) | 0.5 | 25 nM |
| Reverse Primer: R-17-Std or Nest (2 pmol/μl) | 2.5 | 450 nM |
| Template: Temp-F-47(0.01 pmol/μl) | 0.5 | 0.25 nM |
| F-34-Std or F-34-Nest (0.1 pmol/μl) | 0.5 | 2.5 nM |
| R-36-Std or R-36-Nest (0.1 pmol/μl) | 0.5 | 2.5 nM |
| 10 × Reaction Buffer | 2 | 1 × (MgCl$_2$(15 mM) |
| (MgCl$_2$(15 mM) (MgCl$_2$(25 mM) | 0.4 | (MgCl$_2$(0.5 mM) |
| dNTP (2 mM of each dNTP) | 2 | 0.2 mM each |
| dZTP (2 mM) or Water (for negative control) | 2 | 0.2 mM |
| Taq (5 U/μl) | 0.2 | 0.05 U/μl |

Note:
1 × standard Taq Reaction Buffer (10 mM Tris-HCl, 50 nM KCl, 1.5 mM MgCl$_2$, pH 8.3 at 25° C.). 1 × ThermoPol Reaction Buffer (20 mM Tris-HCl, 10 mM(NH$_4$)$_2$SO$_4$, 10 mM KCl, 2 mM MgSO$_4$, 0.1% Tritonx-100, pH 8.8 at 25° C.).

Experiment B used F-34-Std and R-36-Std as chimeric primers. These should generate products when amplified with external primers built without dP, but not when amplification was sought with external primers containing dP. This was in fact the case (FIG. 4, B-Std and B-AEGIS, respectively). Experiment C used F-34-Nest and R-36-Nest as chimeric primers. These should not generate products when amplified with external primers built with dP, but should generate when amplification was sought with external primers containing dP. This was in fact the case (FIG. 4, C-Std and C-AEGIS, respectively). These experiments shows showed the ability of DNA polymerase to support a six letter PCR with dA, dT, dG, dC, dZ, and dP as the six letters. They also demonstrate the orthogonality of the process. Nested PCR works with AEGIS external primers when it should and not when it should not, and vice versa.

Example 3. Primer Extension Through Adjacent dZ in a Template

Given the well-known idiosyncrasies of polymerases and the possibility of strong neighbor effects [Hor95], it was not clear that these results would be extendable to PCR amplifications where dZ or dP are adjacent in a template, requiring the incorporation of dP and dZ adjacent in the template. The following experiments were done to screen thermophilic polymerases for their ability to incorporate dPTP opposite dZ in the template. This was done at the following concentrations: [dATP]=[dCTP]=[dTTP]=100 microM), dGTP (5 microM to 100 microM), or dPTP (5 microM to 100 microM) at pH 7.0 or 7.5, with the following oligonucleotides (R-19-S was P-32 labeled at its 5'-end):

R-19-S:
                                                 SEQ ID 12
5'-GGTACCATCGATACGCGTT-3'

R-36-Nest-6Z:
                                                 SEQ ID 13
3'-CCATGGTAGCTATGCGCAAGTZZTTZZTCGZTAGZG-5'

5'-$^{32}$P-labeled primer R-9-S (2 pmole, final assay concentration 50 nM) was annealed to a template sequence R-36-Nest-6Z (3 pmole, final assay concentration 75 nM) by heating (5 min 95° C.) and then slow cooling (0.5 h) to room temperature, dATP, dTTP and dCTP (4 nmole each, final 100 microM) and dGTP (final 10 microM), or dPTP (final 10 microM) were added at room temperature. The reaction mixture was pre-incubated at 72° C. for 30 seconds and followed by the addition of Taq DNA polymerase to give a final volume of 40 microL. The mixture was incubated at 72° C. for 4 minutes, and quenched by dilution into PAGE loading/quench buffer (10 microL, 10 mM EDTA in formamide). Samples were resolved by electrophoresis using a 14% PAGE (7 M urea). The gel was analyzed using MolecularImager software.

Figure 5:
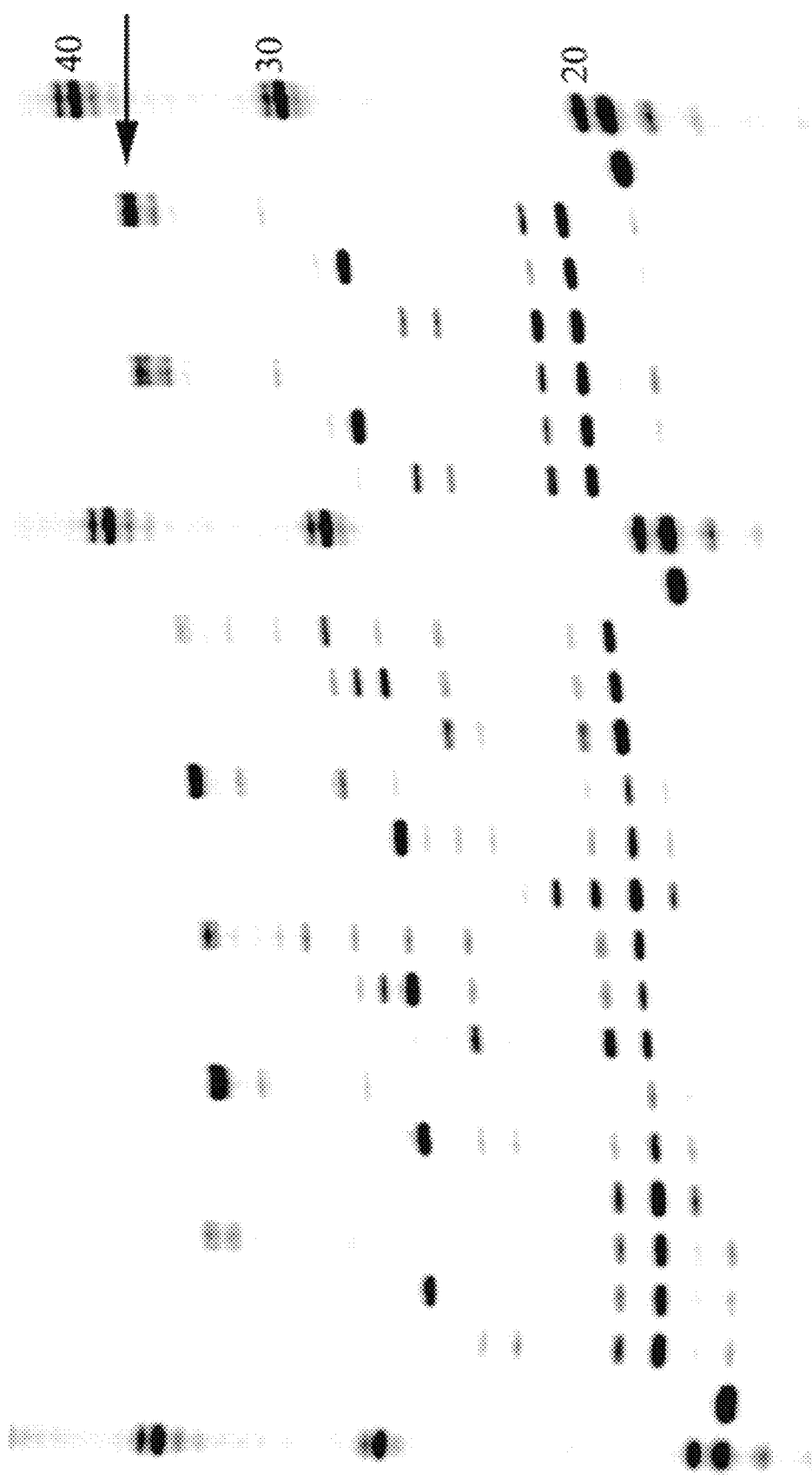
FIG. 5. Autoradiograph of an electrophoresis gel showing primer extension products obtained as described in Example 3 from amplicons containing adjacent dZs.
Figure 6:
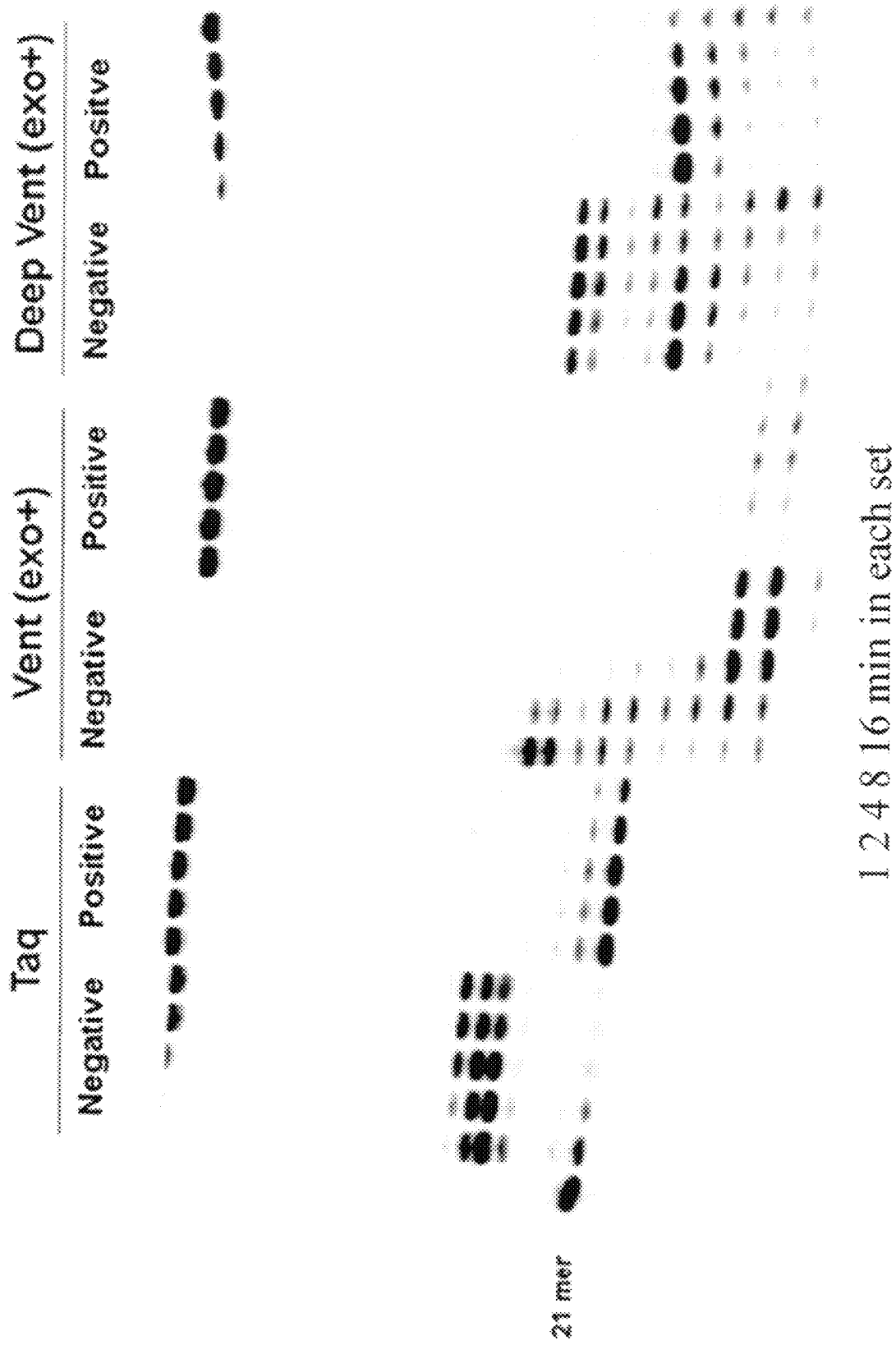
FIG. 6. Autoradiograph of an electrophoresis gel showing primer extension products obtained as described in Example 4.

These results (FIG. 5) showed that Vent and Deep Vent performed better than Taq, Without wishing to be bound by theory, this may be due to their exonuclease activities.

Example 4. Incorporation of dZTP Opposite Consecutive Template dPs

To compare the efficiency and fidelity of DNA polymerases (Taq, Vent (exo+), and DV (exo+)) incorporating dZTP opposite two consecutive dPs in a template, 5-$^{32}$P-labeled primer T7-Y—RS-S16 (0.2 pmole of hot primer plus 4 pmole of cold primer, final assay concentration 70 M) was annealed to template T7-PP-Temp (6 pmole, final assay concentration 100 nM) in 1× Thermopol polymerase reaction buffer (20 mM Tris-HCl, 10 mM (NH$_4$)$_2$SO$_4$, 10 mM KC, 2 mM MgSO$_4$, 0.1% Triton X-100, pH=8.0 at room temperature) by heating (5 min at 95° C.) and then slow cooling (0.5 h) to room temperature, dNTP (each final 0.1 mM) and dZTP (final 0.1 mM, with (+) or without (−)) were added at room temperature. The reaction mixture was cooled to 4° C. for 1 min and followed by the addition of Taq (2.5 units), Vent (exo+), or Deep Vent (exo+) DNA polymerase (2 units for Vent and Deep Vent) to give a final volume of 60 microL. The primer was extended at 65° C. and aliquots (7 microL) were taken from each reaction at time intervals (1, 2, 4, 8, and 16 min), quenched by PAGE loading/quench buffer (7 microL, 10 mM EDTA in formamide) and resolved by electrophoresis using a 16% PAGE (7 M urea). The gel was analyzed using MolecularImager. These oligonucleotides were used (where the asterisk * indicates a phosphorothioate linkage):

```
Negative control (-):
dNTP (each 0.1 mM)

T7-Y-RS-S16:
                                              SEQ ID 14
3'-GAAAT*CACTCCCAATTAAGCG-5'

T7-PP-Temp:
                                              SEQ ID 15
5'-GCGTAATACGACTCACTATAGACGAPPCTACTTTAGTGAGGGTTAA
TTCGC-3'

Positive control (+):
dNTP (each 0.1 mM), and dZTP (0.1 mM)

T7-Y-RS-S16:3':
                                              SEQ ID 14
3'-GAAAT*CACTCCCAATTAAGCG-5'

T7-PP-Temp:
                                              SEQ ID 15
5'-GCGTAATACGACTCACTATAGACGAPPCTACTTTAGTGAGGGTTAA
TTCGC-3'
```

The order of performance of the polymerases tested is Deep Vent (exo+)>Vent (exo+)>Taq. In the absence of dZTP, Deep Vent and Vent misincorporates only one dCTP opposite the first dP. However, Taq can misincorporate dCTP opposite two consecutive dPs, and then keep extending primer. All are better than exo(−) polymerases (not reported in [Yan07]).

Example 5. PCR with Amplicons Containing Multiple Adjacent dPs and dZs

To compare the outcome of PCR with templates containing one or two adjacent dPs, the following oligonucleotides were prepared:

```
T7-Z-RS-S16:
                                              SEQ ID 16
5'GCGTAATACGACTCAC*TATAG-3'
(Template-A)

T7-G-51-Std:
                                              SEQ ID 17
5'-GCGTAATACGACTCACTATAGACGAGCGTACTTTAGTGAGGGTTAA
TTCGC-3'
(Template-B)

T7-P-Temp:
                                              SEQ ID 18
GCGTAATACGACTCACTATAGACGAPCGTACTTTAGTGAGGGTTAATTC
GC-5'
(Template-C)

T7-PP-Temp:
                                              SEQ ID 15
5'-GCGTAATACGACTCACTATAGACGAPPCTACTTTAGTGAGGGTTAA
TTCGC-3'

T7-Y-RS-S16:
                                              SEQ ID 14
3'-GAAAT*CACTCCCAATTAAGCG-5'
```

These were incubated under the following conditions:

| Components | Volume (μl) | Final Concentration |
|---|---|---|
| Nuclease-Free Water (final volume of 40 μl) | 17 | |
| Forward Primer: T7-Z-RS-S16 (10 pmol/μl) | 1 | 0.25 μM |
| Reverse Primer: T7-Y-RS-S16 (10 pmol/μl) | 1 | 0.25 μM |
| Template: Three different Templates (A, B, and C) (0.01 pmol/μl) | 1 + 4 (H2O) | 0.25 nM |
| 10 × Thermopol Buffer (pH = 8.0) | 4 | |
| dNTP (2 mM ) | 4 | 0.2 mM each |
| dZTP (2 mM) | 4 | 0.2 mM |
| dPTP (2 mM) | 4 | 0.2 mM |
| Hot Start Taq (5 U/μl) | 0.5 | 0.06 U/μl |

ThermoPol Reaction Buffer (20 mM Tris-HCl, 10 mM (NH$_4$)$_2$SO$_4$, 10 mM KCl, 2 mM MgSO$_4$, 0.1% Triton X-100, pH 8.0 at 25° C.). PCR: one cycle of 95° C. for 15 min; 26 cycles of 95° C. for 20 s, (55° C. for 30 s. 72° C. for 1 min or 2 min; 72° C. for 5 min; then stored at 4° C.

Figure 7:
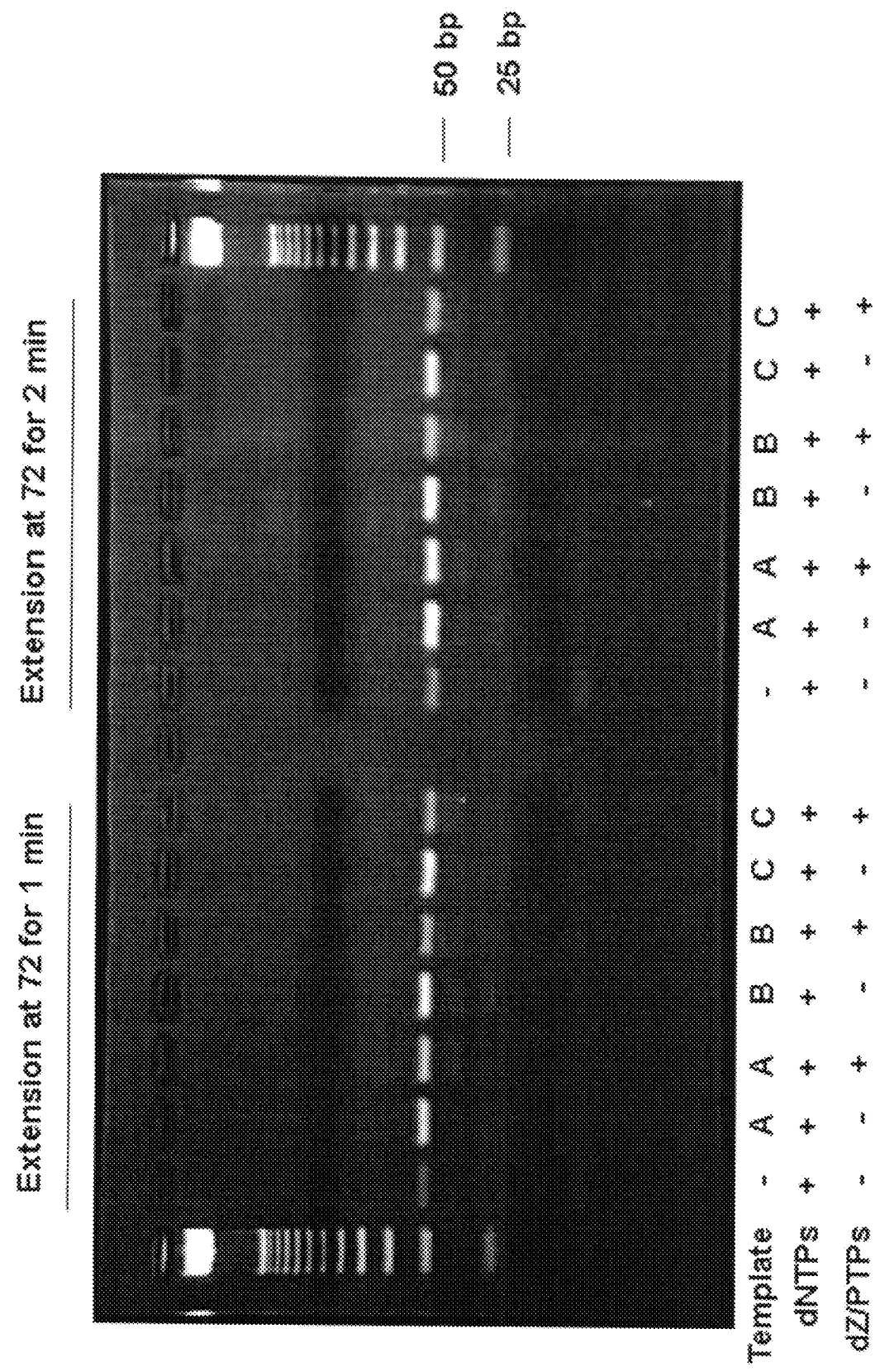
FIG. 7. Autoradiograph of an electrophoresis gel showing PCR products obtained as described in Example 5

The results are shown in FIG. 7. All PCRs generates some degree of 51-mer product. Template A contained only standard nucleotides. Template B contained a single dP. Template C contained a series of dPs, including two adjacent dPs.

Example 6. Prevention of Primer Dimerization with AEGIS Containing Primers

To demonstrate that if dP or dZ were incorporated into PCR primers in place of one or more dGs or dCs, then the synthetic primers containing dPs or dZs would not find their perfectly matched complementary strands in a primer pool, a 17-mer, 5'-CAGGAAGGA<u>GCGATCGC</u>-3'  (SEQ ID 19)

was deliberately designed to form a self-dimer with 8 base pairs at the 3'-end (underline region, $T_m$=32° C.), and subjected to PCR conditions. As expected, primer-dimer formed rapidly. In contrast, perfectly mismatched primers 5'-CAGGAAGGA<u>GCPATCPC</u>-3'  (SEQ ID 20)
and
5'-CAGGAAGGA<u>GZGATZGC</u>-3',  (SEQ ID 21)

which would form primer-dimers only by mismatching dP with dC (in the first case) and dZ with dG (in the second) gave no detectable amplicon under the same conditions, even after 45 cycles.

Example 7. Preferred DNA Polymerases and Optimized Amplification Conditions

With several polymerases able to replicate efficiently DNA fragments containing multiple dPs and dZs, the preferred polymerase having the highest PCR efficiency to amplify target using a nested PCR architecture with AEGIS nucleotides in the external primers was determined. Taq, 9° N, Deep Vent (both exo$^+$ and exo$^-$), Vent (both exo$^+$ and exo$^-$). Phusion. and Herculase were tested; the PCR efficiency was monitored by real-time PCR. The polymerase has the higher PCR efficiency generates more PCR amplicon and producing higher fluorescence signal at an earlier cycle of the PCR. Phusion was found to have the highest PCR efficiency among the polymerases tested with proofreading activity; Deep Vent (exo$^-$) is the most efficient among all the polymerases without exonuclease activity. For all polymerases tested, dP-containing nested PCR, in general, has higher PCR efficiency than that of the dZ-containing nested PCR.

Phusion DNA polymerase generates long templates with an accuracy and speed previously unattainable with a single enzyme. In addition, the error rate of Phusion is 50-fold lower than that of Taq, and about 6-fold lower than that of Vent and Deep Vent. Therefore, Phusion DNA polymerase was further optimized as a presently preferred polymerase for nested PCR with dP-containing external primers. The major infidelity during the 6-nucleotide PCR arises from misincorporation of dGTP opposite template dZs or dZTP opposite template dGs. This infidelity is pH dependent, when the pH of the reaction buffer is low, the rate of misincorporation goes down.

To determine a preferred pH for PCR efficiency and fidelity, three types of nested PCR were conducted with Phusion HF buffer at four different pH values (7.0, 7.5, 8.0, and 8.5). Amplification were monitored by the real-time PCR with SYBR Green. For "type A" nested PCR, standard external and chimeric primers and four standard nucleotide triphosphates (dNTPs) were used; amplification curves in real-time show that PCR efficiency increases when the pH of the buffer decreases. After 30 cycles, the melting temperature of each PCR amplicon was measured and the size of each amplicon was analyzed by agarose (3%) gel. The $T_m$ of each PCR amplicon generated under four different pH values is roughly the same (about 91.49±0.5° C.).

The type B nested PCR is identical to the type A nested PCR, except that dZTP was also included into the reaction. By comparing the melting temperature of each PCR amplicon in the type B reaction with that of the type A reaction, misincorporation of dZTP at different pHs was measured. The $T_m$ of the amplicon improves as the pH of the reaction buffer decreases. For example, at the highest pH value tested (8.5), the $T_m$ of the PCR amplicon is 3.75±0.05° C. below than that of the control PCR (type A); at the lowest pH value (7.0), the $\Delta T_m$ was to 0.29±0.05° C. below the fully standard PCR. For the type C nested PCR, dP-containing primers were used instead of standard primers, and PCR amplifications were conducted under the same conditions as type B nested PCR. The $T_m$ of each PCR amplicon increases as the pH value of the reaction buffer decreases; the effect of pH on PCR efficiency and misincorporation of dZTP opposite template dG agreed with that with type B nested PCR. However, the $T_m$ of each PCR amplicon in the type C nested PCR is higher (about 3.6° C.) than in type B nested PCR, this enhancement of the $T_m$ is mainly due to the higher thermostability of the Z:P base pairs in the PCR amplicon.

The PCR amplicons obtained at four different pHs in type B nested PCR were cloned, and their sequences were verified by Sanger sequencing. This shows that misincorporation of dZTP opposite template G is insignificant does not prevent the PCR amplicon of interest to be cloned and sequenced using the conventional Sanger method. This too was not expected given [Yan07].

Example 8. Nested PCR with AEGIS External Primers Cleans Up Multiplexed PCR

To show whether the dP-containing nested PCR can enhance the capability of multiplexed PCR, this system was applied to human genomic DNA, targeting the three genes associated with cancer: TOP1, HBEGF, and MYC. The oligonucleotides used in this experiment were:

```
Top-F-External
                                         SEQ ID 22
5'-TPTAPATTTPTATPTATPTATPAT-3'

Top-F-Chimeric
                                         SEQ ID 23
5'-TPTAPATTTPTATPTATPTATPATGACAGCCCCGGATGAGAAC-3'

TOP-R-Chimeric
                                         SEQ ID 24
3'-GTTAGCTCGACAACGTTAAGAACAPAGGPAAATPACTCPCA-5'

Universal-R-4P
                                         SEQ ID 25
3'-CAPAGGPAAATPACTCPCA-5'
```

The external primers were adopted from Luminex's 5'-universal tag sequences, which were designed by the company to have unique sequences to avoid cross-hybrdization and have roughly equal melting temperatures. To design the chimeric primers, universal external primer was added to either forward or reverse gene-specific primers, the other three external primers were also attached to gene-specific primers, the combination of each external primer to a certain gene-specific primer was optimized using primer design software (OligoAnalyzer 3.1), and following the general principles of multiplex PCR primer design to avoid cross-hybrdization and hairpin structure of primers.

Figure 8:
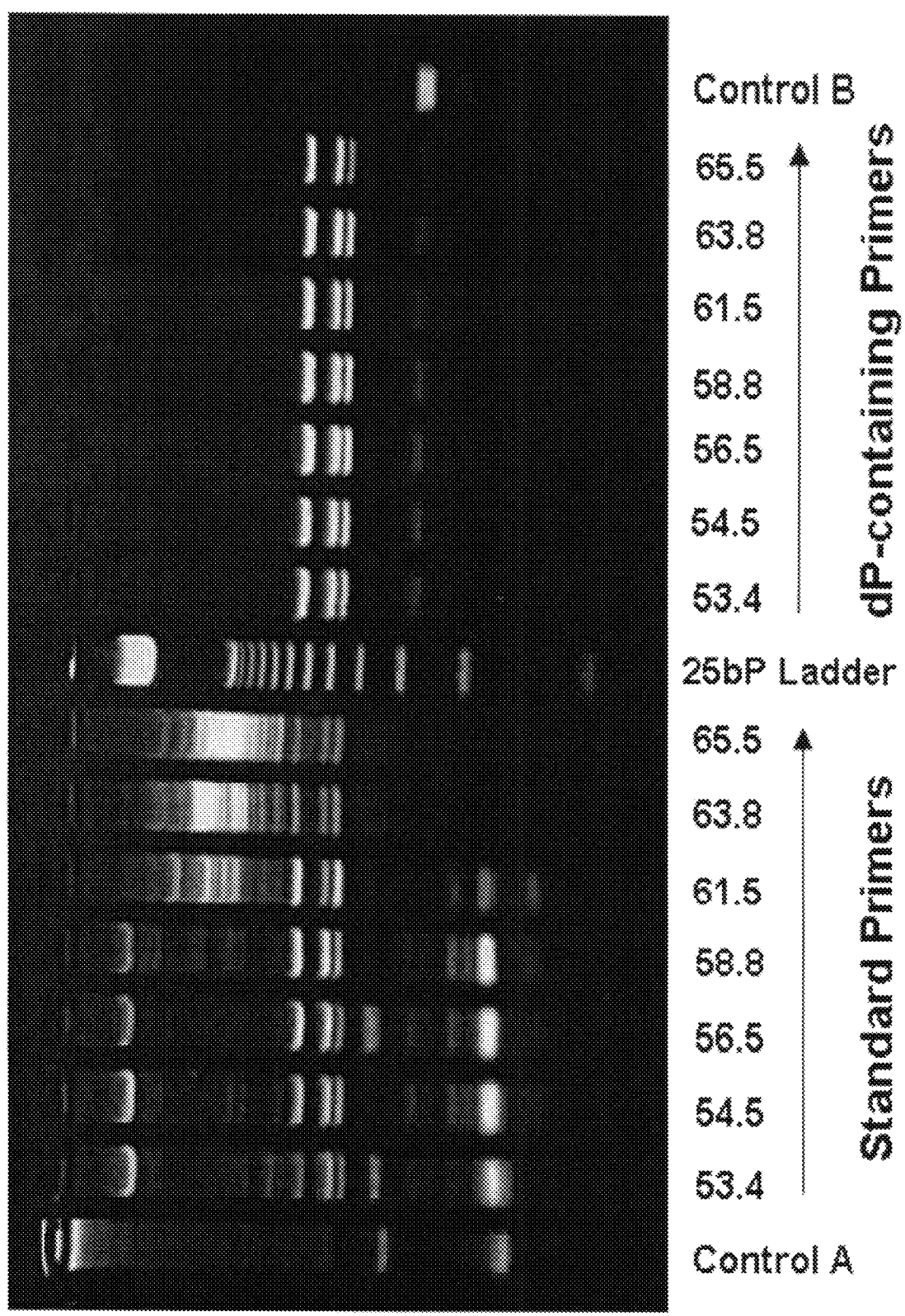
FIG. 8. Autoradiograph of an electrophoresis gel showing that nested PCR external primers containing AEGIS components produces cleaner PCR products (right) than with standard external primers (left).

Three cancer genes in human genomic DNA were multiplexed amplified by standard nested PCR and dP-containing nested PCR using Phusion under seven different annealing temperatures. As shown in FIG. 8, standard nested PCR with all annealing temperatures give messy PCR results (left): at the lower annealing temperatures (from 53.4° C. to 58.8° C.), significant amounts of primer dimer (about 40 nucleotides in length) were generated; at the higher annealing temperatures (from 61.5° C. to 65.5° C.), non-specific PCR artifacts (PCR amplicons longer than the desired length) were produced along with the disappearance of the primer dimer.

However, the dP-containing nested PCR generated the desired PCR amplicons with minimal PCR artifacts (right). For the two control reactions (without genomic DNA), control A (standard nested PCR) gave some primer dimers (about 40 mer amplicon formed by standard external primers) and significant amount of long PCR amplicons, which may caused by the further primering of primer dimer. The control B (dP-containing nested PCR) gave one band, which was formed by the dimerization of the dP-containing chimeric primers, as the 3'-ends of the chimeric primers are the standard gene-specific oligonucleotides. This dimerization could be further eliminated by reducing the concentration of the dP-containing chimeric primers. We further verified that the dP-containing multiplexed nested PCR also performed better than the standard nested PCR under HF Phusion buffer with other different pH values (8.5, 8.0, and 7.5).

This result was entirely unanticipated. Nested PCR using AEGIS external primers leads to cleaner multiplexed PCR. Without wishing to be bound by theory, this may arise because even with standard primers not having exact matched in a genome, standard primers have sufficient mismatches to prime at off-target sites.

| Literature cited | |
|---|---|
| [Bro97] | Brownie, J., Shawcross, S., Theaker, J., Whitcombe, D., Ferrie, R., Newton, C., Little, S. (1997). The elimination of primer-dimer accumulation in PCR. *Nucleic Acids Res.* 25, 3235-3241 |
| [Hor95] | Horlacher,J., Hottiger, M., Podust, V.N., Hübscher, U., Benner, S.A. (1995)Expanding the genetic alphabet: Recognition by viral and cellular DNA polymerases of nucleosides bearing bases with non-standard hydrogen bonding patterns, *Proc. Natl. Acad. Sci.*, 92, 6329-6333 |
| [Hut03] | Hutter, D. and Benner, S. A. (2003) Expanding the genetic alphabet. Non-epimerizing nucleoside with pyDDA hydrogen bonding pattern. *J. Org. Chem.*, 68, 9839-9842 |
| [Swi89] | Switzer, C. Y., Moroney, S.E., Benner, S. A. (1989) Enzymatic incorporation of a new base pair into DNA and RNA. *J. Am. Chem. Soc.* 111, 8322-8323 |
| [Voe96a] | Voegel, J. J., Benner, S. A. (1996) Synthesis and characterization of non-standard nucleosides and nucleotides bearing the acceptor-donor-donor pyrimidine analog 6-amino-3-methylpyrazine-2-one. *Helv. Chim. Acta* 79, 1863-1880 |
| [Voe96b] | Voegel, J. J., Benner, S. A. (1996) Synthesis, molecular recognition and enzymology of oligonucleotides containing the non-standard base pair between 5-aza-7-deaza-iso-guanine and 6-amino-3-methylpyrazine-2-one, a donor-acceptor-acceptor purine analog and an acceptor-donor-donor pyrimidine analog. *Helv. Chim. Acta* 79, 1881-1898 |
| [Voe93] | Voegel, J. J., von Krosigk, U., Benner, S. A. (1993) Synthesis and tautomeric equilibrium of 6-amino-5-benzyl-3-methylpyrazin-2-one. An acceptor-donor-donor nucleoside base analog. *J. Org. Chem.* 58, 7542-7547 |
| [Von95] | von Krosigk, U., Benner, S. A. (1995) pH-independent triple helix formation by an oligonucleotide containing a pyrazine donor-donor-acceptor base, *J. Am. Chem. Soc.* 117, 5361-5362 |
| [Yan06] | Yang, Z., Hutter, D., Sheng, P., Sismour, A. M. and Benner, S. A. (2006) Artificially expanded genetic information system. A new base pair with an alternative hydrogen bonding pattern. *Nucleic Acids Res.*, 34, 6095-6101. |
| [Yan07] | Yang, Z., Sismour, A. M., Sheng, P., Puskar, N. L., Benner, S. A. (2007) Enzymatic incorporation of a third nucleobase pair. *Nucl. Acids. Res.* 35, 4238-4249 |

What is claimed is:

1. A process for creating a DNA molecule that is complementary to a preselected DNA molecule, wherein said process comprises (a) contacting said preselected DNA molecule with a primer under conditions where said primer anneals to said preselected DNA molecule to form a duplex, wherein said preselected DNA molecule contains at least one non-standard nucleotide comprising a nucleobase selected from the group consisting of

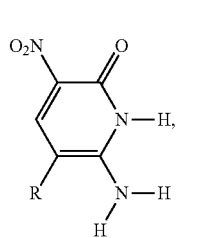
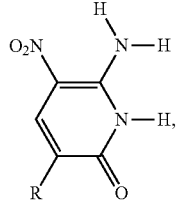

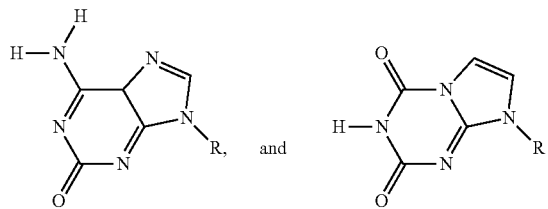

(b) incubating said duplex with an enzyme selected from the group consisting of a DNA polymerase, an RNA polymerase, and a reverse transcriptase, (c) wherein said mixture also contains nucleoside analog triphosphates that are Watson-Crick complementary to the nucleotides in said preselected DNA molecule, and (d) wherein said enzyme incorporates opposite each of the nucleotides in said preselected DNA molecule, wherein R is the point of attachment of said nucleobase to said preselected DNA molecule.

2. The process of claim 1, wherein said nucleobase is

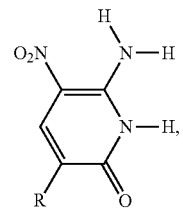

wherein R is the point of attachment of said nucleobase to said preselected DNA molecule.

3. The process of claim 1 wherein said enzyme is selected from the group consisting of Phusion, Vent and Deep Vent.

4. The process of claim 1, wherein the pH is adjusted to optimize the melting temperature of said duplex.

5. The process of claim 4, wherein said pH is between 6.5 and 7.5.

6. The process of claim 1, where multiple segments are amplified at the same time.

7. A process for amplifying an oligonucleotide sequence, said process comprising (a) contacting said sequence in aqueous solution with a forward primer and a reverse primer, wherein said forward primer is complementary to a region at the 3'-end of said sequence, wherein the reverse primer is identical in sequence to a region at the 5'-end of said sequence, (b) incubating said solution with an enzyme selected from the group consisting of a DNA polymerase, an RNA polymerase, and a reverse transcriptase, (c) wherein said mixture also contains nucleoside triphosphates that are Watson-Crick complementary to the nucleotides in said oligonucleotide sequence and its complement, and (d) wherein" said enzyme incorporates a nucleotide from each of said nucleoside triphosphates opposite each of the nucleotides in said sequence and its complement, and wherein said sequence contains at least two non-standard nucleotides incorporating the nucleobase

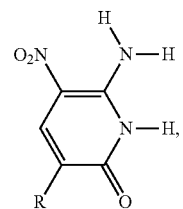

wherein R is the point of attachment of said nucleobase to said preselected DNA molecule.

8. The process of claim 7 wherein said enzyme is selected from the group consisting of Phusion, Vent and Deep Vent.

9. The process of claim 7, wherein the pH is adjusted to optimize the melting temperature of the amplicon duplex.

10. The process of claim 9, wherein said pH is between 6.5 and 7.5.

11. The process of claim 7, wherein said non-standard nucleotides are adjacent in said sequence.

12. A process for creating a DNA molecule that is complementary to a preselected DNA molecule, wherein said process comprises (a) contacting said preselected DNA molecule in aqueous solution with a primer that is not attached to a solid support under conditions where said primer anneals to said preselected DNA molecule to form a duplex, wherein said preselected DNA molecule contains at least one non-standard nucleotide comprising a nucleobase selected from the group consisting of

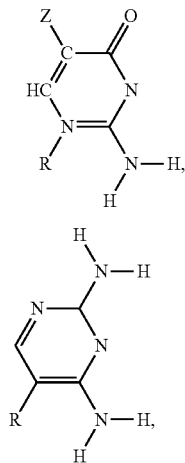
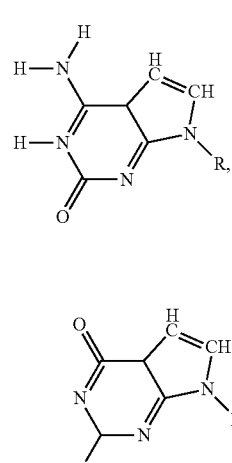
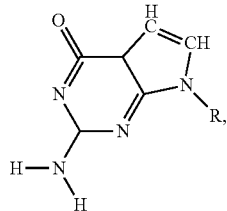 and wherein Z is alkyl, (b) incubating said solution with an enzyme selected from the group consisting of a DNA polymerase, an RNA polymerase, and a reverse transcriptase, (c) wherein said mixture also contains nucleoside analog triphosphates that are Watson-Crick complementary to the nucleotides in said preselected DNA molecule, and (d) wherein said enzyme incorporates opposite each of the nucleotides in said preselected DNA molecule, wherein R is the point of attachment of said nucleobase to said preselected DNA molecule.

13. A process for amplifying an oligonucleotide sequence, said process comprising (a) contacting said sequence in aqueous solution with a forward primer and a reverse primer, wherein said forward primer is complementary to a region at the 3'-end of said sequence, wherein the reverse primer is identical in sequence to a region at the 5'-end of said sequence (b) incubating said solution with an enzyme selected from the group consisting of a DNA polymerase, an RNA polymerase, and a reverse transcriptase, (c) wherein said mixture also contains nucleoside triphosphates that are Watson-Crick complementary to the nucleotides in said oligonucleotide sequence and its complement, (d) wherein said enzyme incorporates a nucleotide from each of said nucleoside triphosphates opposite each of the nucleotides in said sequence and its complement, and (e) wherein said enzyme continues to incorporate nucleotides after incorporating any non-standard nucleotides, wherein said sequence contains at least two non-standard nucleotides comprising the nucleobase

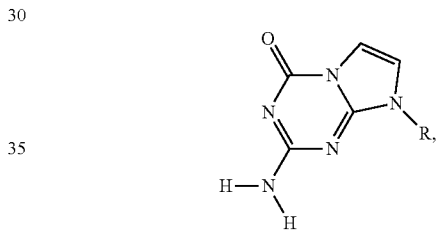

wherein R is the point of attachment of said nucleobase to said preselected DNA molecule.

* * * * *

SEQUENCE LISTING

```
<160> NUMBER OF SEQ ID NOS: 31

<210> SEQ ID NO 1
<211> LENGTH: 36
<212> TYPE: DNA
<213> ORGANISM: Artificial Sequence
<220> FEATURE:
<223> OTHER INFORMATION: Synthetic

<400> SEQUENCE: 1
caggaaggag cgatcgcaac gcgtatcgat ggtacc                          36

<210> SEQ ID NO 2
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2-amino-8-(1'-beta-D-2'-deoxyribofuranosyl)-
      imidazo[1,2a]-1,3,5-triazin-4(8H)-one
```

```
<220> FEATURE:
<221> NAME/KEY: misc_feature
<222> LOCATION: (8)..(8)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (12)..(12)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (16)..(16)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 2
cagnaagnag cnatcncaac gcgtatcgat ggtacc                              36

<210> SEQ ID NO 3
<211> LENGTH: 47
<212> TYPE: DNA
<213> ORGANISM: Artificial Sequence
<220> FEATURE:
<223> OTHER INFORMATION: Synthetic

<400> SEQUENCE: 3
aacgcgtatc gatggtaccc ggccgggccc accgcggtct cccatgg                  47

<210> SEQ ID NO 4
<211> LENGTH: 17
<212> TYPE: DNA
<213> ORGANISM: Artificial Sequence
<220> FEATURE:
<223> OTHER INFORMATION: synthetic

<400> SEQUENCE: 4
caggaaggag cgatcgc                                                   17

<210> SEQ ID NO 5
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (8)..(8)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (12)..(12)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (16)..(16)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 5
cagnaagnag cnatcnc                                                   17

<210> SEQ ID NO 6
<211> LENGTH: 36
```

```
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (6)..(6)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (10)..(11)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (14)..(15)
<223> OTHER INFORMATION: 6-amino-3-(2'-deoxy)-D-ribofuranosyl)-5-nitro-
      1H-pyridin-2-one

<400> SEQUENCE: 6
gngatngctn nttnntgaac gcgtatcgat ggtacc                              36

<210> SEQ ID NO 7
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (17)..(17)
<223> OTHER INFORMATION: thymine phosphorothioate

<400> SEQUENCE: 7
gcgaattaac cctcacnaaa g                                              21

<210> SEQ ID NO 8
<211> LENGTH: 41
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (8)..(8)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (13)..(13)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (17)..(17)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 8
acnctcanta aangganaca agaattgcaa cagctcgatt g                        41

<210> SEQ ID NO 9
```

```
<211> LENGTH: 19
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (8)..(8)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (13)..(13)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (17)..(17)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 9
acnctcanta aangganac                                                  19

<210> SEQ ID NO 10
<211> LENGTH: 42
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (8)..(8)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (13)..(13)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (17)..(17)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 10
acnctcanta aangganacc ggacatactc tgtttggcac tt                        42

<210> SEQ ID NO 11
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (8)..(8)
<223> OTHER INFORMATION: 2-amino-8-(1'-beta-D-2'-deoxyribofuranosyl)-
      imidazo[1,2a]-1,3,5-triazin-4(8H)-one
```

```
<220> FEATURE:
<221> NAME/KEY: misc_feature
<222> LOCATION: (13)..(13)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (17)..(17)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 11
acnctcanta aangganacc cgcgctttga tcaagagtcc                                40

<210> SEQ ID NO 12
<211> LENGTH: 47
<212> TYPE: DNA
<213> ORGANISM: Artificial Sequence
<220> FEATURE:
<223> OTHER INFORMATION: synthetic

<400> SEQUENCE: 12
ccatgggaga ccgcggtggg cccggccggg taccatcgat acgcgtt                       47

<210> SEQ ID NO 13
<211> LENGTH: 34
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (8)..(8)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (12)..(12)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (16)..(16)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 13
ctangacnac gnactnccca tgggagaccg cggt                                     34

<210> SEQ ID NO 14
<211> LENGTH: 34
<212> TYPE: DNA
<213> ORGANISM: Artificial Sequence
<220> FEATURE:
<223> OTHER INFORMATION: synthetic

<400> SEQUENCE: 14
ctaggacgac ggactgccca tgggagaccg cggt                                     34

<210> SEQ ID NO 15
<211> LENGTH: 17
<212> TYPE: DNA
<213> ORGANISM: Artificial Sequence
<220> FEATURE:
<223> OTHER INFORMATION: synthetic
<220> FEATURE:
```

```
<221> NAME/KEY: misc_feature
<222> LOCATION: (4)..(4)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (8)..(8)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (12)..(12)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (16)..(16)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 15
ctangacnac gnactnc                                                    17

<210> SEQ ID NO 16
<211> LENGTH: 17
<212> TYPE: DNA
<213> ORGANISM: Artificial Sequence
<220> FEATURE:
<223> OTHER INFORMATION: synthetic

<400> SEQUENCE: 16
ctaggacgac ggactgc                                                    17

<210> SEQ ID NO 17
<211> LENGTH: 81
<212> TYPE: DNA
<213> ORGANISM: Artificial Sequence
<220> FEATURE:
<223> OTHER INFORMATION: synthetic

<400> SEQUENCE: 17
ctaggacgac ggactgccca tgggagaccg cggtgggccc ggccgggtac catcgatacg     60
cgttgcgatc gctccttcct g                                               81

<210> SEQ ID NO 18
<211> LENGTH: 19
<212> TYPE: DNA
<213> ORGANISM: Artificial Sequence
<220> FEATURE:
<223> OTHER INFORMATION: synthetic

<400> SEQUENCE: 18
ggtaccatcg atacgcgtt                                                  19

<210> SEQ ID NO 19
<211> LENGTH: 51
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (26)..(27)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 19
gcgtaatacg actcactata gacganncta ctttagtgag ggttaattcg c              51
```

```
<210> SEQ ID NO 20
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: cytosine phosphorothioate

<400> SEQUENCE: 20
gcgtaatacg actcantata g                                                21

<210> SEQ ID NO 21
<211> LENGTH: 51
<212> TYPE: DNA
<213> ORGANISM: Artificial Sequence
<220> FEATURE:
<223> OTHER INFORMATION: synthetic

<400> SEQUENCE: 21
gcgtaatacg actcactata gacgagcgta ctttagtgag ggttaattcg c                51

<210> SEQ ID NO 22
<211> LENGTH: 51
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (26)..(26)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 22
gcgtaatacg actcactata gacgancgta ctttagtgag ggttaattcg c                51

<210> SEQ ID NO 23
<211> LENGTH: 17
<212> TYPE: DNA
<213> ORGANISM: Artificial Sequence
<220> FEATURE:
<223> OTHER INFORMATION: synthetic

<400> SEQUENCE: 23
caggaaggag cgatcgc                                                     17

<210> SEQ ID NO 24
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (16)..(16)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 24
caggaaggag cnatcnc                                                     17
```

```
<210> SEQ ID NO 25
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (15)..(15)
<223> OTHER INFORMATION: 6-amino-3-(2'-deoxy)-D-ribofuranosyl)-5-nitro-
      1H-pyridin-2-one

<400> SEQUENCE: 25
caggaaggag ngatngc                                                       17

<210> SEQ ID NO 26
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (5)..(5)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (10)..(10)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (14)..(14)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (18)..(18)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (22)..(22)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 26
tntanatttn tatntatnta tnat                                               24

<210> SEQ ID NO 27
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (5)..(5)
```

```
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (10)..(10)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (14)..(14)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (18)..(18)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (22)..(22)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 27
tntanatttn tatntatnta tnatgacagc cccggatgag aac                    43

<210> SEQ ID NO 28
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (9)..(9)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (13)..(13)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (16)..(16)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (21)..(21)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 28
aaantatant aanatntata ntag                                        24

<210> SEQ ID NO 29
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (9)..(9)
```

```
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (13)..(13)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (16)..(16)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (21)..(21)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 29
aaantatant aanatntata ntagccccag ttgccgtcta gga                43

<210> SEQ ID NO 30
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (9)..(9)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (13)..(13)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (19)..(19)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (23)..(23)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 30
gtatttnant aantaattna ttna                                    24

<210> SEQ ID NO 31
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (9)..(9)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (13)..(13)
```

```
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (19)..(19)
<223> OTHER INFORMATION: 2-amino-8-(1'-beta-D-2'-deoxyribofuranosyl)-
      imidazo[1,2a]-1,3,5-triazin-4(8H)-one
<220> FEATURE:
<221> NAME/KEY: misc_feature
<222> LOCATION: (23)..(23)
<223> OTHER INFORMATION: 2-amino-8-(1'-beta-D-2'-deoxyribofuranosyl)-
      imidazo[1,2a]-1,3,5-triazin-4(8H)-one

<400> SEQUENCE: 31
gtatttnant aantaattna ttnatcctcc ttatgcctct atcat            45
```